(12) United States Patent
Carley et al.

(10) Patent No.: US 7,850,797 B2
(45) Date of Patent: *Dec. 14, 2010

(54) METHODS FOR MANUFACTURING A CLIP AND CLIP

(75) Inventors: Michael T. Carley, San Jose, CA (US); Richard S. Ginn, San Jose, CA (US)

(73) Assignee: Integrated Vascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/403,256

(22) Filed: Mar. 12, 2009

(65) Prior Publication Data

US 2009/0177213 A1 Jul. 9, 2009

Related U.S. Application Data

(63) Continuation of application No. 10/541,083, filed as application No. PCT/US03/40812 on Dec. 17, 2003.

(51) Int. Cl.
C22F 1/00 (2006.01)
A61B 17/08 (2006.01)

(52) U.S. Cl. .................................. 148/563; 606/151
(58) Field of Classification Search .............. 148/559, 148/563

See application file for complete search history.

(56) References Cited

U.S. PATENT DOCUMENTS

| 287,046 A | 10/1883 | Norton |
| 438,400 A | 10/1890 | Brennen |
| 1,088,393 A | 2/1914 | Backus |
| 1,331,401 A | 2/1920 | Summers |
| 1,596,004 A | 8/1926 | De Bengoa |
| 1,647,958 A | 11/1927 | Ciarlante |

(Continued)

FOREIGN PATENT DOCUMENTS

CA 2 339 060 2/2000

(Continued)

OTHER PUBLICATIONS

Stretch Comb by Scuenci, date unavailable but has been sold for at least 10 years.*

(Continued)

*Primary Examiner*—Roy King
*Assistant Examiner*—Vanessa Velasquez
(74) *Attorney, Agent, or Firm*—Workman Nydegger (57) ABSTRACT

The present invention relates to a method of making clips which can be used to engage body tissue for the purpose of closing wounds. Such clips are generally annular in shape and have radially inwardly extending tines. The present invention first forms a precursor which, in one embodiment, has the tines extending radially outwardly from the annular body and then forms the clip by inverting the precursor such that the tines extend radially inwardly. In an alternate embodiment, the precursor is formed with an over-sized lateral dimension and then compressed inwardly to bring the tines closer together and to reduce the lateral dimension of the precursor. It is preferred to manufacture such clips from a superelastic alloy such as nickel-titanium, in which case the inverted or compressed precursor must be heated and quenched to heat set the clip in its final shape.

6 Claims, 5 Drawing Sheets

U.S. PATENT DOCUMENTS

| | | |
|---|---|---|
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A * | 3/1992 | Miura ........................ 148/563 |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |

| | | | | | |
|---|---|---|---|---|---|
| 5,114,065 A | 5/1992 | Storace | 5,411,520 A | 5/1995 | Nash et al. |
| 5,116,349 A | 5/1992 | Aranyi | 5,413,571 A | 5/1995 | Katsaros et al. |
| 5,122,122 A | 6/1992 | Allgood | 5,413,584 A | 5/1995 | Schulze |
| 5,122,156 A | 6/1992 | Granger et al. | 5,416,584 A | 5/1995 | Kay |
| 5,131,379 A | 7/1992 | Sewell, Jr. | 5,417,699 A | 5/1995 | Klein et al. |
| 5,147,381 A | 9/1992 | Heimerl et al. | 5,419,777 A | 5/1995 | Hofling |
| 5,156,609 A | 10/1992 | Nakao et al. | 5,423,857 A | 6/1995 | Rosenman et al. |
| 5,158,566 A | 10/1992 | Pianetti | 5,425,489 A | 6/1995 | Shichman et al. |
| 5,160,339 A | 11/1992 | Chen et al. | 5,425,740 A | 6/1995 | Hutchinson, Jr. |
| 5,167,634 A | 12/1992 | Corrigan, Jr. et al. | 5,431,639 A | 7/1995 | Shaw |
| 5,167,643 A | 12/1992 | Lynn | 5,431,667 A | 7/1995 | Thompson et al. |
| 5,171,249 A | 12/1992 | Stefanchik et al. | 5,433,721 A | 7/1995 | Hooven et al. |
| 5,171,250 A | 12/1992 | Yoon | 5,437,631 A | 8/1995 | Janzen |
| 5,171,251 A | 12/1992 | Bregen et al. | 5,439,479 A | 8/1995 | Shichman et al. |
| 5,176,648 A | 1/1993 | Holmes et al. | 5,443,477 A | 8/1995 | Marin et al. |
| 5,176,682 A | 1/1993 | Chow | 5,443,481 A | 8/1995 | Lee |
| 5,192,288 A | 3/1993 | Thompson et al. | 5,449,359 A | 9/1995 | Groiso |
| 5,192,300 A | 3/1993 | Fowler | 5,456,400 A | 10/1995 | Shichman et al. |
| 5,192,301 A | 3/1993 | Kamiya et al. | 5,462,558 A | 10/1995 | Kolesa et al. |
| 5,192,302 A | 3/1993 | Kensey et al. | 5,462,561 A | 10/1995 | Voda |
| 5,192,602 A | 3/1993 | Spencer et al. | 5,466,241 A | 11/1995 | Leroy et al. |
| 5,203,787 A | 4/1993 | Noblitt et al. | 5,470,010 A | 11/1995 | Rothfuss et al. |
| 5,209,756 A | 5/1993 | Seedhorm et al. | 5,474,557 A | 12/1995 | Mai |
| 5,217,024 A | 6/1993 | Dorsey et al. | 5,474,572 A | 12/1995 | Hayhurst |
| 5,219,359 A | 6/1993 | McQuilkin et al. | 5,478,352 A | 12/1995 | Fowler |
| 5,222,974 A | 6/1993 | Kensey et al. | 5,478,353 A | 12/1995 | Yoon |
| 5,226,908 A | 7/1993 | Yoon | 5,478,354 A | 12/1995 | Tovey et al. |
| 5,234,449 A | 8/1993 | Bruker et al. | 5,486,195 A | 1/1996 | Myers et al. |
| 5,236,435 A | 8/1993 | Sewell, Jr. | 5,497,933 A | 3/1996 | DeFonzo et al. |
| 5,236,445 A | 8/1993 | Hayhurst et al. | 5,501,698 A | 3/1996 | Roth et al. |
| 5,242,457 A | 9/1993 | Akopov et al. | 5,507,744 A | 4/1996 | Tay et al. |
| 5,242,459 A | 9/1993 | Buelna | 5,507,755 A | 4/1996 | Gresl et al. |
| 5,246,156 A | 9/1993 | Rothfuss et al. | 5,514,159 A | 5/1996 | Matula et al. |
| 5,246,443 A | 9/1993 | Mai | 5,521,184 A | 5/1996 | Zimmermann |
| 5,250,058 A | 10/1993 | Miller et al. | 5,522,840 A | 6/1996 | Krajicek |
| 5,254,105 A | 10/1993 | Haaga | 5,527,322 A | 6/1996 | Klein et al. |
| 5,258,015 A | 11/1993 | Li et al. | 5,536,251 A | 7/1996 | Evard et al. |
| 5,269,792 A | 12/1993 | Kovac et al. | 5,540,712 A * | 7/1996 | Kleshinski et al. ......... 623/1.19 |
| 5,275,616 A | 1/1994 | Fowler | 5,540,716 A | 7/1996 | Hlavacek |
| 5,282,808 A | 2/1994 | Kovac et al. | 5,543,520 A | 8/1996 | Zimmermann |
| 5,282,827 A | 2/1994 | Kensey et al. | 5,544,802 A | 8/1996 | Crainich |
| 5,282,832 A | 2/1994 | Toso et al. | 5,547,474 A | 8/1996 | Kloeckl et al. |
| 5,289,963 A | 3/1994 | McGarry et al. | 5,560,532 A | 10/1996 | DeFonzo et al. |
| 5,290,243 A | 3/1994 | Chodorow et al. | 5,571,120 A | 11/1996 | Yoon |
| 5,290,310 A | 3/1994 | Makower et al. | 5,575,771 A | 11/1996 | Walinsky |
| 5,292,309 A | 3/1994 | Van Tassel et al. | 5,584,879 A | 12/1996 | Reimold et al. |
| 5,292,332 A | 3/1994 | Lee | 5,591,205 A | 1/1997 | Fowler |
| 5,304,184 A | 4/1994 | Hathaway et al. | 5,593,412 A | 1/1997 | Martinez et al. |
| 5,304,204 A | 4/1994 | Bregen | 5,593,422 A | 1/1997 | Muijs Van der Moer et al. |
| 5,306,254 A | 4/1994 | Nash et al. | 5,593,425 A | 1/1997 | Bonutti et al. |
| 5,306,280 A | 4/1994 | Bregen et al. | 5,601,602 A | 2/1997 | Fowler |
| 5,318,542 A | 6/1994 | Hirsch et al. | 5,609,597 A | 3/1997 | Lehrer |
| 5,320,639 A | 6/1994 | Rudnick | 5,611,986 A | 3/1997 | Datta et al. |
| 5,330,442 A | 7/1994 | Green et al. | 5,613,974 A | 3/1997 | Andreas et al. |
| 5,330,445 A | 7/1994 | Haaga | 5,618,291 A | 4/1997 | Thompson et al. |
| 5,334,216 A | 8/1994 | Vidal et al. | 5,618,306 A | 4/1997 | Roth et al. |
| 5,334,217 A | 8/1994 | Das | 5,620,452 A | 4/1997 | Yoon |
| 5,335,680 A * | 8/1994 | Moore ....................... 132/276 | 5,620,461 A | 4/1997 | Muijs et al. |
| 5,340,360 A | 8/1994 | Stefanchik | 5,630,824 A | 5/1997 | Hart |
| 5,350,399 A | 9/1994 | Erlebacher et al. | 5,643,318 A | 7/1997 | Tsukernik et al. |
| 5,352,229 A | 10/1994 | Goble et al. | 5,645,553 A | 7/1997 | Kolesa et al. |
| 5,364,406 A | 11/1994 | Sewell, Jr. | 5,645,565 A | 7/1997 | Rudd et al. |
| 5,364,408 A | 11/1994 | Gordon | 5,645,566 A | 7/1997 | Brenneman et al. |
| 5,366,458 A | 11/1994 | Korthoff et al. | 5,645,567 A | 7/1997 | Crainich |
| 5,366,479 A | 11/1994 | McGarry et al. | 5,649,959 A | 7/1997 | Hannam et al. |
| 5,376,101 A | 12/1994 | Green et al. | D383,539 S | 9/1997 | Croley |
| 5,383,896 A | 1/1995 | Gershony et al. | 5,669,917 A | 9/1997 | Sauer et al. |
| 5,383,905 A | 1/1995 | Golds et al. | 5,674,231 A | 10/1997 | Green et al. |
| RE34,866 E | 2/1995 | Kensey et al. | 5,676,689 A | 10/1997 | Kensey et al. |
| 5,391,173 A | 2/1995 | Wilk | 5,676,974 A | 10/1997 | Valdes et al. |
| 5,392,978 A | 2/1995 | Velez et al. | 5,681,334 A | 10/1997 | Evans et al. |
| 5,395,030 A | 3/1995 | Kuramoto et al. | 5,681,351 A | 10/1997 | Jamiolkowski et al. |
| 5,409,499 A | 4/1995 | Yi | 5,683,405 A | 11/1997 | Yacoubian et al. |

| | | | | | |
|---|---|---|---|---|---|
| 5,690,674 A | 11/1997 | Diaz | 5,910,155 A | 6/1999 | Ratcliff et al. |
| 5,695,504 A | 12/1997 | Gifford, III et al. | 5,919,207 A | 7/1999 | Taheri |
| 5,695,505 A | 12/1997 | Yoon | 5,919,208 A | 7/1999 | Valenti |
| 5,695,524 A | 12/1997 | Kelley et al. | 5,922,009 A | 7/1999 | Epstein et al. |
| 5,700,273 A | 12/1997 | Buelna et al. | 5,935,147 A | 8/1999 | Kensey et al. |
| 5,709,708 A | 1/1998 | Thal | 5,938,667 A | 8/1999 | Peyser et al. |
| 5,716,375 A | 2/1998 | Fowler | 5,941,890 A | 8/1999 | Voegele et al. |
| 5,720,755 A | 2/1998 | Dakov | 5,947,999 A | 9/1999 | Groiso |
| 5,720,765 A | 2/1998 | Thal | 5,951,518 A | 9/1999 | Licata et al. |
| 5,725,498 A | 3/1998 | Janzen et al. | 5,951,576 A | 9/1999 | Wakabayashi |
| 5,725,552 A | 3/1998 | Kotula et al. | 5,951,589 A | 9/1999 | Epstein et al. |
| 5,725,554 A | 3/1998 | Simon et al. | 5,957,936 A | 9/1999 | Yoon et al. |
| 5,725,556 A | 3/1998 | Moser et al. | 5,957,938 A | 9/1999 | Zhu et al. |
| 5,728,109 A | 3/1998 | Schulze et al. | 5,964,782 A | 10/1999 | Lafontaine et al. |
| 5,728,110 A | 3/1998 | Vidal et al. | 5,976,159 A | 11/1999 | Bolduc et al. |
| 5,728,114 A | 3/1998 | Evans et al. | 5,976,161 A | 11/1999 | Kirsch et al. |
| 5,728,122 A | 3/1998 | Leschinsky et al. | 5,984,934 A | 11/1999 | Ashby et al. |
| 5,728,132 A | 3/1998 | Van Tassel et al. | 5,984,949 A | 11/1999 | Levin |
| 5,732,872 A | 3/1998 | Bolduc et al. | 5,993,468 A | 11/1999 | Rygaard |
| 5,735,873 A | 4/1998 | MacLean | 5,993,476 A | 11/1999 | Groiso |
| 5,735,875 A | 4/1998 | Bonutti et al. | 6,001,110 A | 12/1999 | Adams |
| 5,735,877 A | 4/1998 | Pagedas | 6,004,341 A | 12/1999 | Zhu et al. |
| 5,749,898 A | 5/1998 | Schulze et al. | 6,007,563 A | 12/1999 | Nash et al. |
| 5,752,966 A | 5/1998 | Chang | 6,013,084 A | 1/2000 | Ken et al. |
| 5,755,726 A | 5/1998 | Pratt et al. | 6,022,372 A | 2/2000 | Kontos |
| 5,755,778 A | 5/1998 | Kleshinski | 6,024,750 A | 2/2000 | Mastri |
| 5,766,217 A | 6/1998 | Christy | 6,024,758 A | 2/2000 | Thal |
| 5,766,246 A | 6/1998 | Mulhauser et al. | 6,030,364 A | 2/2000 | Durgin et al. |
| 5,769,862 A | 6/1998 | Kammerer et al. | 6,030,413 A | 2/2000 | Lazarus |
| 5,769,870 A | 6/1998 | Salahieh et al. | 6,033,427 A | 3/2000 | Lee |
| 5,776,150 A | 7/1998 | Nolan et al. | 6,036,703 A | 3/2000 | Evans et al. |
| 5,779,707 A | 7/1998 | Bertholet et al. | 6,036,720 A | 3/2000 | Abrams et al. |
| 5,782,844 A | 7/1998 | Yoon et al. | 6,045,570 A | 4/2000 | Epstein et al. |
| 5,782,860 A | 7/1998 | Epstein et al. | 6,048,358 A | 4/2000 | Barak |
| 5,782,861 A | 7/1998 | Cragg et al. | 6,056,768 A | 5/2000 | Cates et al. |
| 5,782,864 A | 7/1998 | Lizardi | 6,056,769 A | 5/2000 | Epstein et al. |
| 5,795,958 A | 8/1998 | Rao et al. | 6,056,770 A | 5/2000 | Epstein et al. |
| 5,797,928 A | 8/1998 | Kogasaka | 6,059,800 A | 5/2000 | Hart et al. |
| 5,797,931 A | 8/1998 | Bito et al. | 6,063,085 A | 5/2000 | Tay et al. |
| 5,797,933 A | 8/1998 | Snow et al. | 6,063,114 A | 5/2000 | Nash et al. |
| 5,797,958 A | 8/1998 | Yoon | 6,066,160 A | 5/2000 | Colvin et al. |
| 5,810,776 A | 9/1998 | Bacich et al. | 6,071,300 A | 6/2000 | Brenneman et al. |
| 5,810,846 A | 9/1998 | Virnich et al. | 6,074,409 A | 6/2000 | Goldfarb |
| 5,810,851 A | 9/1998 | Yoon | 6,077,281 A | 6/2000 | Das |
| 5,810,877 A | 9/1998 | Roth et al. | 6,077,291 A | 6/2000 | Das |
| 5,814,069 A | 9/1998 | Schulze et al. | 6,080,182 A | 6/2000 | Shaw et al. |
| 5,817,113 A | 10/1998 | Gifford, III et al. | 6,080,183 A | 6/2000 | Tsugita et al. |
| 5,820,631 A | 10/1998 | Nobles | 6,086,608 A | 7/2000 | Ek et al. |
| 5,827,298 A | 10/1998 | Hart et al. | 6,090,130 A | 7/2000 | Nash et al. |
| 5,830,125 A | 11/1998 | Scribner et al. | 6,092,561 A | 7/2000 | Schmid |
| 5,833,698 A | 11/1998 | Hinchliffe et al. | 6,099,553 A | 8/2000 | Hart et al. |
| 5,843,167 A | 12/1998 | Dwyer et al. | 6,102,271 A | 8/2000 | Longo et al. |
| 5,846,254 A | 12/1998 | Schulze et al. | 6,106,545 A | 8/2000 | Egan |
| 5,853,421 A | 12/1998 | Leschinsky et al. | 6,110,184 A | 8/2000 | Weadock |
| 5,853,422 A | 12/1998 | Huebsch et al. | 6,113,612 A | 9/2000 | Swanson et al. |
| 5,855,312 A | 1/1999 | Toledano | 6,117,125 A | 9/2000 | Rothbarth et al. |
| 5,858,082 A * | 1/1999 | Cruz et al. .................. 106/644 | 6,117,148 A | 9/2000 | Ravo |
| 5,860,991 A | 1/1999 | Klein et al. | 6,120,524 A | 9/2000 | Taheri |
| 5,861,005 A | 1/1999 | Kontos | 6,126,675 A | 10/2000 | Schervinsky et al. |
| 5,868,755 A | 2/1999 | Kanner et al. | 6,126,677 A | 10/2000 | Ganaja et al. |
| 5,868,763 A | 2/1999 | Spence et al. | 6,136,010 A | 10/2000 | Modesitt et al. |
| 5,871,474 A | 2/1999 | Hermann et al. | 6,143,017 A | 11/2000 | Thal |
| 5,871,490 A | 2/1999 | Schulze et al. | 6,149,660 A | 11/2000 | Laufer et al. |
| 5,871,501 A | 2/1999 | Leschinsky et al. | 6,149,667 A | 11/2000 | Hovland et al. |
| 5,871,525 A | 2/1999 | Edwards et al. | 6,152,144 A | 11/2000 | Lesh et al. |
| 5,873,876 A | 2/1999 | Christy | 6,152,934 A | 11/2000 | Harper et al. |
| 5,879,366 A | 3/1999 | Shaw et al. | 6,152,936 A | 11/2000 | Christy et al. |
| 5,893,592 A | 4/1999 | Schulze et al. | 6,152,937 A * | 11/2000 | Peterson et al. ............. 606/153 |
| 5,897,487 A | 4/1999 | Ouchi | 6,159,234 A | 12/2000 | Bonutti et al. |
| 5,902,310 A | 5/1999 | Foerster et al. | 6,165,204 A | 12/2000 | Levinson et al. |
| 5,904,697 A | 5/1999 | Gifford, III et al. | 6,174,324 B1 | 1/2001 | Egan et al. |
| 5,906,631 A | 5/1999 | Imran | 6,193,734 B1 | 2/2001 | Bolduc et al. |
| 5,907,893 A | 6/1999 | Zadno-Azizi et al. | 6,197,042 B1 | 3/2001 | Ginn et al. |

| | | | | | | |
|---|---|---|---|---|---|---|
| 6,200,329 B1 | 3/2001 | Fung et al. | | 6,712,836 B1 | 3/2004 | Berg et al. |
| 6,203,565 B1 | 3/2001 | Bonutti et al. | | 6,719,777 B2 * | 4/2004 | Ginn et al. ............... 606/213 |
| 6,206,913 B1 | 3/2001 | Yencho et al. | | 6,726,704 B1 | 4/2004 | Loshakove et al. |
| 6,220,248 B1 | 4/2001 | Voegele et al. | | 6,743,195 B2 | 6/2004 | Zucker |
| 6,221,102 B1 | 4/2001 | Baker et al. | | 6,743,243 B1 | 6/2004 | Roy et al. |
| 6,231,592 B1 | 5/2001 | Bonutti et al. | | 6,743,259 B2 | 6/2004 | Ginn |
| 6,248,124 B1 | 6/2001 | Pedros et al. | | 6,749,621 B2 | 6/2004 | Pantages et al. |
| 6,254,615 B1 | 7/2001 | Bolduc et al. | | 6,749,622 B2 | 6/2004 | McGuckin et al. |
| 6,254,617 B1 | 7/2001 | Spence et al. | | 6,755,842 B2 | 6/2004 | Kanner et al. |
| 6,254,642 B1 | 7/2001 | Taylor | | 6,767,356 B2 | 7/2004 | Kanner et al. |
| 6,277,140 B2 | 8/2001 | Ginn et al. | | 6,780,197 B2 | 8/2004 | Roe et al. |
| 6,280,460 B1 | 8/2001 | Bolduc et al. | | 6,837,906 B2 | 1/2005 | Ginn |
| 6,287,322 B1 | 9/2001 | Zhu et al. | | 6,846,319 B2 | 1/2005 | Ginn et al. |
| 6,296,657 B1 | 10/2001 | Brucker | | 6,890,343 B2 | 5/2005 | Ginn et al. |
| 6,305,891 B1 | 10/2001 | Burlingame | | 6,896,687 B2 | 5/2005 | Dakov |
| 6,319,258 B1 | 11/2001 | McAllen, III et al. | | 6,896,692 B2 | 5/2005 | Ginn et al. |
| 6,322,580 B1 | 11/2001 | Kanner | | 6,926,723 B1 | 8/2005 | Mulhauser et al. |
| 6,334,865 B1 | 1/2002 | Redmond et al. | | 6,926,731 B2 | 8/2005 | Coleman et al. |
| 6,348,064 B1 | 2/2002 | Kanner | | 6,942,674 B2 | 9/2005 | Belef et al. |
| 6,358,258 B1 | 3/2002 | Arcia et al. | | 6,942,691 B1 | 9/2005 | Chuter |
| D457,958 S | 5/2002 | Dycus | | 6,964,668 B2 | 11/2005 | Modesitt et al. |
| 6,383,208 B1 | 5/2002 | Sancoff et al. | | 6,969,397 B2 | 11/2005 | Ginn |
| 6,391,048 B1 | 5/2002 | Ginn et al. | | 6,989,003 B2 | 1/2006 | Wing et al. |
| 6,395,015 B1 | 5/2002 | Borst et al. | | 6,989,016 B2 | 1/2006 | Tallarida et al. |
| 6,398,752 B1 | 6/2002 | Sweezer et al. | | 7,001,398 B2 | 2/2006 | Carley et al. |
| 6,402,765 B1 | 6/2002 | Monassevitch et al. | | 7,001,400 B1 | 2/2006 | Modesitt et al. |
| 6,409,739 B1 | 6/2002 | Nobles et al. | | 7,008,435 B2 | 3/2006 | Cummins |
| 6,419,669 B1 | 7/2002 | Frazier et al. | | 7,008,439 B1 | 3/2006 | Janzen et al. |
| 6,423,054 B1 | 7/2002 | Ouchi | | 7,033,379 B2 | 4/2006 | Peterson |
| 6,428,472 B1 | 8/2002 | Haas | | 7,060,084 B1 | 6/2006 | Loshakove et al. |
| 6,428,548 B1 | 8/2002 | Durgin et al. | | 7,063,711 B1 | 6/2006 | Loshakove et al. |
| 6,443,158 B1 | 9/2002 | Lafontaine et al. | | 7,083,635 B2 | 8/2006 | Ginn |
| 6,443,963 B1 | 9/2002 | Baldwin et al. | | 7,108,709 B2 | 9/2006 | Cummins |
| 6,447,540 B1 | 9/2002 | Fontaine et al. | | 7,108,710 B2 | 9/2006 | Anderson |
| 6,450,391 B1 | 9/2002 | Kayan et al. | | 7,111,768 B2 | 9/2006 | Cummins et al. |
| 6,458,130 B1 | 10/2002 | Frazier et al. | | 7,112,225 B2 | 9/2006 | Ginn |
| 6,461,364 B1 | 10/2002 | Ginn et al. | | 7,144,411 B2 | 12/2006 | Ginn et al. |
| 6,482,224 B1 | 11/2002 | Michler et al. | | 7,163,551 B2 | 1/2007 | Anthony et al. |
| 6,488,692 B1 | 12/2002 | Spence et al. | | 7,169,158 B2 | 1/2007 | Sniffin et al. |
| 6,500,115 B2 | 12/2002 | Krattiger et al. | | 7,169,164 B2 | 1/2007 | Borillo et al. |
| 6,506,210 B1 | 1/2003 | Kanner | | 7,211,101 B2 | 5/2007 | Carley et al. |
| 6,517,569 B2 | 2/2003 | Mikus et al. | | 7,316,704 B2 | 1/2008 | Bagaoisan et al. |
| 6,533,762 B2 | 3/2003 | Kanner et al. | | 7,326,230 B2 | 2/2008 | Ravikumar |
| 6,533,812 B2 | 3/2003 | Swanson et al. | | 7,331,979 B2 | 2/2008 | Khosravi et al. |
| 6,537,288 B2 | 3/2003 | Vargas et al. | | 7,335,220 B2 | 2/2008 | Khosravi et al. |
| 6,547,806 B1 | 4/2003 | Ding | | D566,272 S | 4/2008 | Walberg et al. |
| 6,569,173 B1 | 5/2003 | Blatter et al. | | 7,361,183 B2 | 4/2008 | Ginn |
| 6,569,185 B2 | 5/2003 | Ungs | | 7,361,185 B2 | 4/2008 | O'Malley et al. |
| 6,572,629 B2 | 6/2003 | Kalloo et al. | | 7,393,363 B2 | 7/2008 | Ginn |
| 6,582,452 B2 | 6/2003 | Coleman et al. | | 7,396,359 B1 | 7/2008 | Derowe et al. |
| 6,582,482 B2 | 6/2003 | Gillman et al. | | 7,533,790 B2 | 5/2009 | Knodel et al. |
| 6,599,303 B1 | 7/2003 | Peterson et al. | | 7,597,706 B2 | 10/2009 | Kanner et al. |
| 6,602,263 B1 | 8/2003 | Swanson et al. | | D611,144 S | 3/2010 | Reynolds |
| 6,610,072 B1 | 8/2003 | Christy et al. | | 2001/0007077 A1 | 7/2001 | Ginn et al. |
| 6,613,059 B2 | 9/2003 | Schaller et al. | | 2001/0031972 A1 | 10/2001 | Robertson et al. |
| 6,616,686 B2 | 9/2003 | Coleman et al. | | 2001/0046518 A1 | 11/2001 | Sawhney |
| 6,623,509 B2 | 9/2003 | Ginn | | 2001/0047180 A1 | 11/2001 | Grudem et al. |
| 6,623,510 B2 * | 9/2003 | Carley et al. ............... 606/213 | | 2002/0026208 A1 | 2/2002 | Roe et al. |
| 6,626,918 B1 | 9/2003 | Ginn et al. | | 2002/0026215 A1 | 2/2002 | Redmond et al. |
| 6,632,238 B2 | 10/2003 | Ginn et al. | | 2002/0038127 A1 | 3/2002 | Blatter et al. |
| 6,634,537 B2 | 10/2003 | Chen | | 2002/0042622 A1 | 4/2002 | Vargas et al. |
| 6,645,205 B2 | 11/2003 | Ginn | | 2002/0049427 A1 | 4/2002 | Wiener et al. |
| 6,652,538 B2 | 11/2003 | Kayan et al. | | 2002/0049472 A1 | 4/2002 | Coleman et al. |
| 6,652,556 B1 | 11/2003 | VanTassel et al. | | 2002/0058960 A1 | 5/2002 | Hudson et al. |
| 6,663,655 B2 | 12/2003 | Ginn et al. | | 2002/0072768 A1 | 6/2002 | Ginn |
| 6,669,714 B2 | 12/2003 | Coleman et al. | | 2002/0077657 A1 | 6/2002 | Ginn et al. |
| 6,676,671 B2 | 1/2004 | Robertson et al. | | 2002/0082641 A1 | 6/2002 | Ginn et al. |
| 6,676,685 B2 | 1/2004 | Pedros et al. | | 2002/0099389 A1 | 7/2002 | Michler et al. |
| 6,679,904 B2 | 1/2004 | Gleeson et al. | | 2002/0106409 A1 | 8/2002 | Sawhney et al. |
| 6,689,147 B1 | 2/2004 | Koster, Jr. | | 2002/0107542 A1 | 8/2002 | Kanner et al. |
| 6,695,867 B2 | 2/2004 | Ginn et al. | | 2002/0133193 A1 | 9/2002 | Ginn et al. |
| 6,699,256 B1 | 3/2004 | Logan et al. | | 2002/0151921 A1 | 10/2002 | Kanner et al. |
| 6,702,826 B2 | 3/2004 | Liddicoat et al. | | 2002/0188318 A1 * | 12/2002 | Carley et al. ............... 606/213 |

| | | |
|---|---|---|
| 2002/0193808 A1 | 12/2002 | Belef et al. |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0032981 A1 | 2/2003 | Kanner et al. |
| 2003/0065358 A1 | 4/2003 | Frecker et al. |
| 2003/0078598 A1 | 4/2003 | Pantages et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0158577 A1 | 8/2003 | Ginn et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092964 A1 | 5/2004 | Modesitt et al. |
| 2004/0092968 A1 | 5/2004 | Caro et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0165357 A1 | 7/2005 | McGuckin et al. |
| 2005/0177189 A1 | 8/2005 | Ginn et al. |
| 2005/0216057 A1 | 9/2005 | Coleman et al. |
| 2005/0222614 A1 | 10/2005 | Ginn et al. |
| 2005/0234508 A1 | 10/2005 | Cummins et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0034930 A1 | 2/2006 | Khosravi et al. |
| 2006/0047313 A1 | 3/2006 | Khanna et al. |
| 2006/0100664 A1 | 5/2006 | Pai et al. |
| 2006/0135989 A1 | 6/2006 | Carley et al. |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0253037 A1 | 11/2006 | Ginn et al. |
| 2006/0253072 A1 | 11/2006 | Pai et al. |
| 2006/0265012 A1 | 11/2006 | Anderson |
| 2006/0287674 A1 | 12/2006 | Ginn et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0123817 A1 | 5/2007 | Khosravi et al. |
| 2007/0203506 A1 | 8/2007 | Sibbitt, Jr. et al. |
| 2007/0250080 A1 | 10/2007 | Jones et al. |
| 2007/0270904 A1 | 11/2007 | Ginn |
| 2007/0276416 A1 | 11/2007 | Ginn et al. |
| 2007/0282352 A1 | 12/2007 | Carley et al. |
| 2008/0004636 A1 | 1/2008 | Walberg |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0210737 A1 | 9/2008 | Ginn et al. |
| 2008/0221616 A1 | 9/2008 | Ginn et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0312666 A1 | 12/2008 | Ellingwood et al. |
| 2008/0312686 A1 | 12/2008 | Ellingwood |
| 2008/0319475 A1 | 12/2008 | Clark |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0177212 A1 | 7/2009 | Carley et al. |
| 2009/0230168 A1 | 9/2009 | Coleman et al. |
| 2009/0254119 A1 | 10/2009 | Sibbitt, Jr. et al. |
| 2010/0130965 A1 | 5/2010 | Sibbitt, Jr. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |

| | | |
|---|---|---|
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2008/031102 | 3/2008 |
| WO | WO 2009/079091 | 6/2009 |
| WO | WO 2010/031050 | 3/2010 |
| ZA | 200100527 | 1/2001 |
| ZA | 200100528 | 1/2001 |

OTHER PUBLICATIONS

U.S. Appl. No. 09/478,179, mailed Nov. 6, 2000, Notice of Allowance.
U.S. Appl. No. 09/478,179, mailed Feb. 15, 2001, Issue Notification.
U.S. Appl. No. 09/546,998, mailed May 6, 2002, Notice of Allowance.
U.S. Appl. No. 09/546,998, mailed Sep. 19, 2002, Issue Notification.
U.S. Appl. No. 09/610,238, mailed Mar. 26, 2001, Notice of Allowance.
U.S. Appl. No. 09/610,238, mailed Sep. 5, 2001, Office Action.
U.S. Appl. No. 09/610,238, mailed Feb. 11, 2002, Notice of Allowance.
U.S. Appl. No. 09/610,238, mailed May 3, 2002, Issue Notification.
U.S. Appl. No. 09/732,178, mailed Aug. 1, 2002, Office Action.
U.S. Appl. No. 09/732,178, mailed Dec. 24, 2002, Office Action.
U.S. Appl. No. 09/732,178, mailed Jun. 10, 2003, Office Action.
U.S. Appl. No. 09/732,178, mailed Jul. 3, 2003, Office Action.
U.S. Appl. No. 09/732,178, mailed Nov. 17, 2003, Notice of Allowance.
U.S. Appl. No. 09/732,178, ,mailed Mar. 25, 2004, Issue Notification.
U.S. Appl. No. 09/732,835, mailed Sep. 11, 2003, Office Action.
U.S. Appl. No. 09/732,835, ,mailed Feb. 9, 2004, Office Action.
U.S. Appl. No. 09/732,835, mailed Mar. 17, 2004, Notice of Allowance.
U.S. Appl. No. 09/764,813, mailed Mar. 26, 2001, Office Action.
U.S. Appl. No. 09/764,813, mailed Jun. 4, 2001, Notice of Allowance.
U.S. Appl. No. 09/764,813, mailed Aug. 6, 2001, Issue Notification.
U.S. Appl. No. 09/933,299, mailed Feb. 26, 2003, Office Action.
U.S. Appl. No. 09/933,299, mailed Jun. 16, 2003, Notice of Allowance.
U.S. Appl. No. 09/933,299, mailed Sep. 25, 2003, Issue Notification.
U.S. Appl. No. 09/948,813, mailed Jan. 31, 2003, Notice of Allowance.
U.S. Appl. No. 09/948,813, mailed Jun. 5, 2003, Issue Notification.
U.S. Appl. No. 09/949,398, mailed Mar. 4, 2003, Office Action.
U.S. Appl. No. 09/949,398, mailed Jul. 28, 2003, Notice of Allowance.
U.S. Appl. No. 09/949,398, mailed Dec. 11, 2003, Issue Notification.
U.S. Appl. No. 09/949,438, mailed Dec. 17, 2002, Office Action.
U.S. Appl. No. 09/949,438, mailed Apr. 21, 2003, Notice of Allowance.
U.S. Appl. No. 09/949,438, mailed Aug. 21, 2003, Issue Notification.
U.S. Appl. No. 10/006,400, mailed Aug. 27, 2004, Office Action.
U.S. Appl. No. 10/006,400, mailed Feb. 23, 2005, Office Action.
U.S. Appl. No. 10/006,400, mailed Apr. 11, 2005, Office Action.
U.S. Appl. No. 10/006,400, mailed Jul. 27, 2005, Office Action.
U.S. Appl. No. 10/006,400, mailed Mar. 6, 2006, Office Action.
U.S. Appl. No. 10/006,400, mailed May 24, 2006, Office Action.
U.S. Appl. No. 10/006,400, mailed Oct. 26, 2006, Office Action.

U.S. Appl. No. 10/006,400, mailed Apr. 19, 2007, Office Action.
U.S. Appl. No. 10/006,400, mailed Apr. 2, 2008, Office Action.
U.S. Appl. No. 10/006,400, mailed Jan. 2, 2009, Office Action.
U.S. Appl. No. 10/081,717, mailed Sep. 29, 2003, Notice of Allowance.
U.S. Appl. No. 10/081,717, mailed Feb. 5, 2004, Issue Notification.
U.S. Appl. No. 10/081,723, mailed Sep. 29, 2004, Office Action.
U.S. Appl. No. 10/081,723, mailed May 13, 2005, Notice of Allowance.
U.S. Appl. No. 10/081,725, mailed Feb. 9, 2004, Notice of Allowance.
U.S. Appl. No. 10/081,725, mailed Apr. 13, 2004, Office Action.
U.S. Appl. No. 10/081,725, mailed May 27, 2004, Issue Notification.
U.S. Appl. No. 10/081,726, mailed Apr. 11, 2003, Notice of Allowance.
U.S. Appl. No. 10/081,726, mailed Jun. 9, 2003, Office Action.
U.S. Appl. No. 10/081,726, mailed Sep. 4, 2003, Issue Notification.
U.S. Appl. No. 10/147,774, mailed Nov. 4, 2004, Office Action.
U.S. Appl. No. 10/147,774, mailed May 4, 2005, Office Action.
U.S. Appl. No. 10/147,774, mailed Oct. 18, 2005, Office Action.
U.S. Appl. No. 10/147,774, mailed Apr. 18, 2007, Notice of Allowance.
U.S. Appl. No. 10/147,774, mailed Sep. 27, 2007, Notice of Allowance.
U.S. Appl. No. 10/147,774, mailed Feb. 4, 2008, Notice of Allowance.
U.S. Appl. No. 10/147,774, mailed Jun. 30, 2008, Office Action.
U.S. Appl. No. 10/240,183, mailed Jul. 27, 2004, Office Action.
U.S. Appl. No. 10/240,183, mailed Dec. 17, 2004, Office Action.
U.S. Appl. No. 10/240,183, mailed Mar. 9, 2005, Notice of Allowance.
U.S. Appl. No. 10/240,183, mailed Aug. 11, 2006, Office Action.
U.S. Appl. No. 10/264,306, mailed Feb. 9, 2005, Office Action.
U.S. Appl. No. 10/264,306, mailed May 26, 2005, Office Action.
U.S. Appl. No. 10/264,306, mailed Oct. 4, 2005, Office Action.
U.S. Appl. No. 10/264,306, mailed May 10, 2006, Notice of Allowance.
U.S. Appl. No. 10/264,306, mailed Jul. 2, 2007, Notice of Allowance.
U.S. Appl. No. 10/264,306, mailed Feb. 4, 2008, Notice of Allowance.
U.S. Appl. No. 10/264,306, mailed Jun. 27, 2008, Office Action.
U.S. Appl. No. 10/264,306, mailed Feb. 26, 2009, Office Action.
U.S. Appl. No. 10/305,923, mailed Nov. 1, 2004, Office Action.
U.S. Appl. No. 10/305,923, mailed Mar. 3, 2005, Notice of Allowance.
U.S. Appl. No. 10/335,075, mailed Aug. 10, 2005, Office Action.
U.S. Appl. No. 10/335,075, mailed Dec. 19, 2005, Office Action.
U.S. Appl. No. 10/335,075, mailed Apr. 21, 2006, Office Action.
U.S. Appl. No. 10/335,075, mailed Dec. 27, 2006, Notice of Allowance.
U.S. Appl. No. 10/335,075, mailed Apr. 11, 2007, Issue Notification.
U.S. Appl. No. 10/356,214, mailed Nov. 30, 2005, Office Action.
U.S. Appl. No. 10/356,214, mailed Aug. 23, 2006, Office Action.
U.S. Appl. No. 10/356,214, mailed Feb. 13, 2007, Office Action.
U.S. Appl. No. 10/356,214, mailed Sep. 12, 2007, Office Action.
U.S. Appl. No. 10/356,214, mailed Mar. 6, 2008, Office Action.
U.S. Appl. No. 10/356,214, mailed Nov. 4, 2008, Office Action.
U.S. Appl. No. 10/435,104, mailed Jun. 10, 2004, Office Action.
U.S. Appl. No. 10/435,104, mailed Sep. 21, 2004, Notice of Allowance.
U.S. Appl. No. 10/435,104, mailed Jan. 3, 2006, Office Action.
U.S. Appl. No. 10/435,104, mailed Feb. 15, 2006, Issue Notification.
U.S. Appl. No. 10/435,104, mailed May 16, 2006, Office Action.
U.S. Appl. No. 10/435,104, mailed Dec. 28, 2006, Notice of Allowance.
U.S. Appl. No. 10/435,104, mailed May 23, 2007, Issue Notification.
U.S. Appl. No. 10/435,104, mailed Jul. 10, 2007, Notice of Allowance.
U.S. Appl. No. 10/435,104, mailed Aug. 2, 2007, Notice of Allowance.
U.S. Appl. No. 10/435,104, mailed Oct. 26, 2007, Notice of Allowance.
U.S. Appl. No. 10/435,104, mailed Nov. 14, 2007, Notice of Allowance.
U.S. Appl. No. 10/435,104, mailed Apr. 4, 2008, Office Action.
U.S. Appl. No. 10/435,104, mailed Sep. 26, 2008, Office Action.
U.S. Appl. No. 10/435,104, mailed Dec. 22, 2008, Notice of Allowance.
U.S. Appl. No. 10/455,768, mailed Nov. 16, 2004, Office Action.
U.S. Appl. No. 10/455,768, mailed Apr. 6, 2005, Notice of Allowance.
U.S. Appl. No. 10/486,067, mailed Jan. 10, 2006, Office Action.
U.S. Appl. No. 10/486,067, mailed Sep. 20, 2006, Notice of Allowance.
U.S. Appl. No. 10/486,067, mailed Dec. 27, 2006, Issue Notification.
U.S. Appl. No. 10/486,070, mailed Apr. 20, 2005, Office Action.
U.S. Appl. No. 10/486,070, mailed Aug. 10, 2005, Office Action.
U.S. Appl. No. 10/486,070, mailed Oct. 18, 2005, Notice of Allowance.
U.S. Appl. No. 10/517,004, mailed Aug. 13, 2007, Office Action.
U.S. Appl. No. 10/517,004, mailed Jan. 30, 2008, Office Action.
U.S. Appl. No. 10/517,004, mailed Aug. 13, 2008, Notice of Allowance.
U.S. Appl. No. 10/517,004, mailed Feb. 10, 2009, Notice of Allowance.
U.S. Appl. No. 10/517,004, mailed Mar. 24, 2009, Notice of Allowance.
U.S. Appl. No. 10/519,778, mailed Feb. 23, 2006, Office Action.
U.S. Appl. No. 10/519,778, mailed May 31, 2006, Notice of Allowance.
U.S. Appl. No. 10/541,083, mailed Oct. 16, 2007, Office Action.
U.S. Appl. No. 10/541,083, mailed Oct. 31, 2007, Office Action.
U.S. Appl. No. 10/541,083, mailed May 5, 2008, Office Action.
U.S. Appl. No. 10/541,083, mailed Sep. 19, 2008, Notice of Allowance.
U.S. Appl. No. 10/541,083, mailed Dec. 29, 2008, Notice of Allowance.
U.S. Appl. No. 10/616,832, mailed Jun. 30, 2006, Office Action.
U.S. Appl. No. 10/616,832, mailed Oct. 20, 2006, Office Action.
U.S. Appl. No. 10/616,832, mailed May 29, 2007, Office Action.
U.S. Appl. No. 10/616,832, mailed Jan. 22, 2008, Office Action.
U.S. Appl. No. 10/616,832, mailed Sep. 17, 2008, Office Action.
U.S. Appl. No. 10/617,090, mailed Mar. 22, 2005, Office Action.
U.S. Appl. No. 10/617,090, mailed Jul. 6, 2005, Notice of Allowance.
U.S. Appl. No. 10/617,090, mailed Oct. 5, 2005, Notice of Allowance.
U.S. Appl. No. 10/617,090, mailed Feb. 21, 2006, Issue Notification.
U.S. Appl. No. 10/638,115, mailed Sep. 22, 2006, Office Action.
U.S. Appl. No. 10/638,115, mailed Jan. 31, 2007, Office Action.
U.S. Appl. No. 10/638,115, mailed Sep. 18, 2007, Office Action.
U.S. Appl. No. 10/638,115, mailed Feb. 7, 2008, Office Action.
U.S. Appl. No. 10/638,115, mailed Oct. 29, 2008, Office Action.
U.S. Appl. No. 10/667,144, mailed Sep. 19, 2006, Office Action.
U.S. Appl. No. 10/667,144, mailed May 2, 2007, Office Action.
U.S. Appl. No. 10/667,144, mailed Nov. 19, 2007, Office Action.
U.S. Appl. No. 10/667,144, mailed Dec. 5, 2007, Office Action.
U.S. Appl. No. 10/667,144, mailed May 12, 2008, Office Action.
U.S. Appl. No. 10/682,459, mailed Sep. 15, 2006, Office Action.
U.S. Appl. No. 10/682,459, mailed Apr. 18, 2007, Office Action.
U.S. Appl. No. 10/682,459, mailed Apr. 2, 2008, Office Action.
U.S. Appl. No. 10/682,459, mailed Dec. 4, 2008, Office Action.
U.S. Appl. No. 10/786,444, mailed Oct. 30, 2006, Office Action.
U.S. Appl. No. 10/786,444, mailed Apr. 17, 2007, Office Action.
U.S. Appl. No. 10/786,444, mailed Aug. 31, 2007, Office Action.
U.S. Appl. No. 10/786,444, mailed Apr. 24, 2008, Office Action.
U.S. Appl. No. 10/786,444, mailed Oct. 17, 2008, Office Action.
U.S. Appl. No. 10/787,073, mailed Nov. 30, 2006, Office Action.
U.S. Appl. No. 10/787,073, mailed Sep. 5, 2007, Office Action.
U.S. Appl. No. 10/787,073, mailed Feb. 22, 2008, Office Action.
U.S. Appl. No. 10/787,073, mailed Nov. 12, 2008, Office Action.
U.S. Appl. No. 10/908,721, mailed Oct. 19, 2006, Office Action.
U.S. Appl. No. 10/908,721, mailed Aug. 10, 2007, Office Action.
U.S. Appl. No. 10/908,721, mailed Jan. 25, 2008, Office Action.
U.S. Appl. No. 10/908,721, mailed Nov. 25, 2008, Office Action.
U.S. Appl. No. 11/113,549, mailed Feb. 6, 2007, Office Action.

U.S. Appl. No. 11/113,549, mailed May 30, 2007, Office Action.
U.S. Appl. No. 11/113,549, mailed Nov. 9, 2007, Office Action.
U.S. Appl. No. 11/113,549, mailed Apr. 16, 2008, Office Action.
U.S. Appl. No. 11/152,562, mailed May 13, 2008, Office Action.
U.S. Appl. No. 11/152,562, mailed Feb. 13, 2009, Office Action.
U.S. Appl. No. 11/198,811, mailed Aug. 26, 2008, Office Action.
U.S. Appl. No. 11/344,793, mailed Jan. 22, 2009, Office Action.
U.S. Appl. No. 11/344,891, mailed Apr. 29, 2008, Office Action.
U.S. Appl. No. 11/344,891, mailed Dec. 8, 2008, Office Action.
U.S. Appl. No. 11/344,891, mailed Feb. 26, 2009, Office Action.
U.S. Appl. No. 11/396,731, mailed Feb. 13, 2009, Office Action.
U.S. Appl. No. 11/406,203, mailed May 14, 2007, Office Action.
U.S. Appl. No. 11/406,203, mailed Jan. 29, 2008, Notice of Allowance.
U.S. Appl. No. 11/406,203, mailed May 23, 2008, Notice of Allowance.
U.S. Appl. No. 11/406,203, mailed Sep. 22, 2008, Notice of Allowance.
U.S. Appl. No. 11/411,925, mailed Jun. 6, 2007, Office Action.
U.S. Appl. No. 11/411,925, mailed Feb. 5, 2008, Office Action.
U.S. Appl. No. 11/411,925, mailed Jan. 12, 2009, Office Action.
U.S. Appl. No. 11/427,297, mailed Jan. 30, 2009, Office Action.
U.S. Appl. No. 11/461,323, mailed May 2, 2007, Office Action.
U.S. Appl. No. 11/461,323, mailed Oct. 29, 2007, Office Action.
U.S. Appl. No. 11/461,323, mailed Apr. 25, 2008, Office Action.
U.S. Appl. No. 11/461,323, mailed Nov. 6, 2008, Office Action.
U.S. Appl. No. 11/744,089, mailed Nov. 26, 2008, Office Action.
U.S. Appl. No. 12/106,928, mailed Jan. 23, 2009, Office Action.
U.S. Appl. No. 29/296,370, mailed Aug. 18, 2008, Office Action.
U.S. Appl. No. 29/296,370, mailed Dec. 2, 2008, Notice of Allowance.
U.S. Appl. No. 12/113,092, filed Apr. 30, 2008, Ginn et al.
U.S. Appl. No. 60/696,069, filed Jul. 1, 2005, Pantages et al.
U.S. Appl. No. 60/946,026, filed Jun. 25, 2007, Ellingwood.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
"Hand tool for forming telephone connections—comprises pliers with reciprocably driven ram crimping clip around conductors against anvil", Derwent-ACC-No. 1978-B8090A.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.

Jeremy L Gilbert PHD, Wound Closure Biomaterials and Devices, Shock., Mar. 1999, p. 226, vol. 11—No. 3, Institution Northwestern University (editorial review only).
Jochen T. Cremer, MD, et al, Different approaches for minimally invasive closure of atrial septal defects, Ann Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
McCarthy, et al., "Tension (Stay) Suture Bridge", J. of International College of Surgeons, 34(5), pp. 613-614 (Nov. 1960).
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Stretch Comb by Scunci, retrieved via internet at www.scunci.com/productdetail on Oct. 9, 2007, publication date unavailable.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 60/693,531, filed Jun. 24, 2005, Carly.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 61/097,072, filed Sep. 15, 2008, Sibbitt, Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/393,877, filed Feb. 26, 2009, Ellingwood et al.
U.S. Appl. No. 12/481,377, filed Jun. 9, 2009, Clark.
U.S. Appl. No. 12/642,319, filed Dec. 18, 2009, Clark.

Marshall A.C., Lock J.E., Structural and Compliant Anatomy of the Patent Foramen Ovale in Patients Undergoing Transcatheter Closure, Am Heart J Aug. 2000; 140(2); pp. 303-307.

Taber's Cyclopedic Medical Dictionary, 18th Ed. 1997, pp. 747 and 1420.

U.S. Appl. No. 09/680,837, mailed Jul. 9, 2002, Office Action.
U.S. Appl. No. 09/680,837, mailed Nov. 6, 2002, Office Action.
U.S. Appl. No. 09/680,837, mailed Mar. 25, 2003, Office Action.
U.S. Appl. No. 09/680,837, mailed Jun. 16, 2003, Notice of Allowance.
U.S. Appl. No. 09/680,837, mailed Sep. 11, 2003, Issue Notification.
U.S. Appl. No. 10/006,400, mailed Jul. 9, 2009, Notice of Allowance.
U.S. Appl. No. 10/006,400, mailed Jan. 13, 2010, Notice of Allowance.
U.S. Appl. No. 10/006,400, mailed Apr. 27, 2010, Notice of Allowance.
U.S. Appl. No. 10/147,774, mailed Mar. 18, 2009, Office Action.
U.S. Appl. No. 10/147,774, mailed Oct. 26, 2009, Office Action.
U.S. Appl. No. 10/147,774, mailed Jun. 8, 2010, Office Action.
U.S. Appl. No. 10/264,306, mailed Aug. 13, 2009, Office Action.
U.S. Appl. No. 10/264,306, mailed Jan. 27, 2010, Office Action.
U.S. Appl. No. 10/264,306, mailed Jun. 15, 2010, Office Action.
U.S. Appl. No. 10/356,214, mailed Apr. 29, 2009, Office Action.
U.S. Appl. No. 10/356,214, mailed Jan. 13, 2010, Notice of Allowance.
U.S. Appl. No. 10/356,214, mailed May 13, 2010, Notice of Allowance.
U.S. Appl. No. 10/435,104, mailed Jan. 20, 2010, Notice of Allowance.
U.S. Appl. No. 10/435,104, mailed Jun. 2, 2010, Office Action.
U.S. Appl. No. 10/517,004, mailed Jun. 26, 2009, Notice of Allowance.
U.S. Appl. No. 10/517,004, mailed Jan. 11, 2010, Notice of Allowance.
U.S. Appl. No. 10/517,004, mailed Apr. 23, 2010, Notice of Allowance.
U.S. Appl. No. 10/541,083, mailed Apr. 16, 2009, Notice of Allowance.
U.S. Appl. No. 10/541,083, mailed Sep. 30, 2009, Notice of Allowance.
U.S. Appl. No. 10/541,083, mailed Feb. 5, 2010, Notice of Allowance.
U.S. Appl. No. 10/541,083, mailed May 10, 2010, Notice of Allowance.
U.S. Appl. No. 10/616,832, mailed Jul. 21, 2009, Office Action.
U.S. Appl. No. 10/616,832, mailed Jan. 11, 2010, Notice of Allowance.
U.S. Appl. No. 10/616,832, mailed May 12, 2010, Notice of Allowance.
U.S. Appl. No. 10/638,115, mailed May 7, 2009, Notice of Allowance.
U.S. Appl. No. 10/638,115, mailed Dec. 1, 2009, Notice of Allowance.
U.S. Appl. No. 10/638,115, mailed Apr. 2, 2010, Notice of Allowance.
U.S. Appl. No. 10/667,144, mailed Mar. 24, 2009, Office Action.
U.S. Appl. No. 10/667,144, mailed Nov. 23, 2009, Office Action.
U.S. Appl. No. 10/667,144, mailed Jun. 22, 2010, Office Action.
U.S. Appl. No. 10/669,313, mailed Jan. 11, 2006, Notice of Allowance.
U.S. Appl. No. 10/669,313, mailed Jun. 28, 2006, Notice of Allowance.
U.S. Appl. No. 10/669,313, mailed Nov. 15, 2006, Issue Notification.
U.S. Appl. No. 10/682,459, mailed Jun. 10, 2009, Office Action.
U.S. Appl. No. 10/682,459, mailed Dec. 23, 2009, Office Action.
U.S. Appl. No. 10/682,459, mailed Apr. 28, 2010, Office Action.
U.S. Appl. No. 10/786,444, mailed Jun. 18, 2009, Office Action.
U.S. Appl. No. 10/786,444, mailed Jan. 14, 2010, Office Action.
U.S. Appl. No. 10/787,073, mailed Aug. 13, 2009, Office Action.
U.S. Appl. No. 10/787,073, mailed Feb. 17, 2010, Notice of Allowance.
U.S. Appl. No. 10/908,721, mailed Jun. 23, 2009, Office Action.
U.S. Appl. No. 10/908,721, mailed Feb. 2, 2010, Office Action.
U.S. Appl. No. 11/048,503, mailed Mar. 13, 2009, Office Action.
U.S. Appl. No. 11/048,503, mailed Jun. 26, 2009, Office Action.
U.S. Appl. No. 11/048,503, mailed Jan. 11, 2010, Notice of Allowance.
U.S. Appl. No. 11/048,503, mailed Apr. 26, 2010, Notice of Allowance.
U.S. Appl. No. 11/113,549, mailed Jul. 21, 2009, Office Action.
U.S. Appl. No. 11/152,562, mailed Jul. 6, 2009, Office Action.
U.S. Appl. No. 11/152,562, mailed Mar. 31, 2010, Office Action.
U.S. Appl. No. 11/198,811, mailed Sep. 22, 2009, Office Action.
U.S. Appl. No. 11/198,811, mailed Jun. 29, 2010, Notice of Allowance.
U.S. Appl. No. 11/316,775, mailed Apr. 16, 2008, Office Action.
U.S. Appl. No. 11/316,775, mailed Aug. 6, 2008, Office Action.
U.S. Appl. No. 11/344,868, mailed Mar. 25, 2009, Office Action.
U.S. Appl. No. 11/344,891, mailed Oct. 7, 2009, Office Action.
U.S. Appl. No. 11/344,891, mailed May 7, 2010, Office Action.
U.S. Appl. No. 11/390,586, mailed Jun. 24, 2009, Office Action.
U.S. Appl. No. 11/390,586, mailed Jul. 6, 2010, Office Action.
U.S. Appl. No. 11/396,141, mailed May 22, 2009, Office Action.
U.S. Appl. No. 11/396,141, mailed Aug. 26, 2009, Office Action.
U.S. Appl. No. 11/396,141, mailed May 4, 2010, Office Action.
U.S. Appl. No. 11/396,731, mailed May 22, 2009, Office Action.
U.S. Appl. No. 11/396,731, mailed Jun. 29, 2010, Office Action.
U.S. Appl. No. 11/406,203, mailed Mar. 3, 2009, Office Action.
U.S. Appl. No. 11/406,203, mailed Sep. 16, 2009, Office Action.
U.S. Appl. No. 11/406,203, mailed Jun. 18, 2010, Notice of Allowance.
U.S. Appl. No. 11/411,925, mailed Sep. 10, 2009, Office Action.
U.S. Appl. No. 11/427,297, mailed Sep. 15, 2009, Office Action.
U.S. Appl. No. 11/455,993, mailed Feb. 17, 2009, Office Action.
U.S. Appl. No. 11/455,993, mailed Dec. 16, 2009, Office Action.
U.S. Appl. No. 11/508,656, mailed Dec. 9, 2009, Office Action.
U.S. Appl. No. 11/508,656, mailed Mar. 25, 2010, Office Action.
U.S. Appl. No. 11/508,662, mailed Dec. 28, 2009, Office Action.
U.S. Appl. No. 11/508,662, mailed Apr. 14, 2010, Office Action.
U.S. Appl. No. 11/508,715, mailed Jan. 6, 2010, Office Action.
U.S. Appl. No. 11/508,715, mailed Apr. 26, 2010, Office Action.
U.S. Appl. No. 11/532,325, mailed Feb. 23, 2009, Office Action.
U.S. Appl. No. 11/532,325, mailed Jun. 17, 2009, Office Action.
U.S. Appl. No. 11/532,325, mailed Jan. 5, 2010, Office Action.
U.S. Appl. No. 11/532,576, mailed Mar. 1, 2010, Office Action.

U.S. Appl. No. 11/532,576, mailed Apr. 23, 2010, Office Action.
U.S. Appl. No. 11/674,930, mailed Jan. 8, 2009, Office Action.
U.S. Appl. No. 11/674,930, mailed Jun. 4, 2009, Office Action.
U.S. Appl. No. 11/674,930, mailed Jan. 8, 2010, Office Action.
U.S. Appl. No. 11/675,462, mailed Dec. 10, 2009, Office Action.
U.S. Appl. No. 11/744,089, mailed Aug. 14, 2009, Office Action.
U.S. Appl. No. 11/767,818, mailed Dec. 24, 2009, Office Action.
U.S. Appl. No. 11/767,818, mailed Mar. 22, 2010, Office Action.
U.S. Appl. No. 11/852,190, mailed Jun. 24, 2010, Office Action.
U.S. Appl. No. 11/958,295, mailed Aug. 27, 2009, Office Action.
U.S. Appl. No. 11/958,295, mailed May 25, 2010, Office Action.
U.S. Appl. No. 11/959,334, mailed Aug. 19, 2009, Office Action.
U.S. Appl. No. 11/959,334, mailed Jan. 12, 2010, Notice of Allowance.
U.S. Appl. No. 11/959,334, mailed Apr. 14, 2010, Notice of Allowance.
U.S. Appl. No. 12/106,928, mailed Oct. 5, 2009, Office Action.
U.S. Appl. No. 12/106,928, mailed May 10, 2010, Office Action.
U.S. Appl. No. 12/106,937, mailed Mar. 30, 2009, Office Action.
U.S. Appl. No. 12/106,937, mailed Nov. 18, 2009, Office Action.
U.S. Appl. No. 12/113,851, mailed Apr. 27, 2010, Office Action.
U.S. Appl. No. 12/113,851, mailed Jun. 24, 2010, Office Action.
U.S. Appl. No. 12/402,398, mailed Mar. 9, 2010, Office Action.
U.S. Appl. No. 12/402,398, mailed May 20, 2010, Office Action.
U.S. Appl. No. 29/296,370, mailed Apr. 1, 2009, Notice of Allowance.
U.S. Appl. No. 29/296,370, mailed Feb. 10, 2010, Issue Notification.
U.S. Appl. No. 10/435,104, mailed Jul. 23, 2009, Notice of Allowance.
U.S. Appl. No. 10/669,313, mailed Oct. 31, 2005, Office Action.
U.S. Appl. No. 11/048,503, mailed Jul. 30, 2010, Notice of Allowance.
U.S. Appl. No. 11/113,549, mailed Jul. 6, 2010, Office Action.
U.S. Appl. No. 11/959,334, mailed Jul. 23, 2010, Notice of Allowance.
U.S. Appl. No. 12/403,277, mailed Jul. 8, 2010, Office Action.

* cited by examiner

METHODS FOR MANUFACTURING A CLIP AND CLIP

CROSS-REFERENCE TO RELATED APPLICATIONS

This application is a continuation of U.S. patent application Ser. No. 10/541,083, filed Jun. 29, 2005, and entitled "Methods for Manufacturing a Clip and Clip," which is a National Stage Application under 35 U.S.C. §371 of PCT/US03/40812, filed Dec. 17, 2003, and entitled "Methods for Manufacturing a Clip and Clip," which claims the benefit of U.S. patent application Ser. No. 10/335,075, filed Dec. 31, 2002, and entitled "Methods for Manufacturing a Clip and Clip," the entireties of which are hereby incorporated by reference. This application incorporates U.S. Pat. No. 4,665,906, issued May 19, 1987, and entitled "Medical Devices Incorporating SimAlloy Elements;" U.S. Pat. No. 6,719,777, issued Apr. 13, 2004, and entitled "Closure Device and Methods for Making and Using Them;" U.S. patent application Ser. No. 10/081,273, filed Feb. 21, 2002, and entitled "Multiple Use Handle Support for Distributing Forces;" U.S. patent application Ser. No. 10/081,726, filed Feb. 21, 2002, and entitled "Closure Device and Methods for Making and Using Them;" and U.S. patent application Ser. No. 10/081,717, filed Feb. 21, 2002, and entitled "Plunger Apparatus and Methods for Delivering a Closure Device," the entireties of which are incorporated herein by reference.

BACKGROUND OF THE INVENTION

1. The Field of the Invention

The use of certain types of clips, which are initially generally planar and which are deformed to non-planar configuration prior to use, to close openings through tissue, e.g., into body lumens, and more particularly to close a puncture made to gain access to a blood vessel or other body lumen is known. Such clips are generally annular and have tines extending radially from an annular body. For example, such clips are disclosed in the aforementioned co-pending applications and in published PCT Applications WO/99/62408, WO/00/56223 and WO/00/56227, the disclosures of which are incorporated by reference herein. Various methods, e.g., stamping, laser cutting, chemical etching and the like have been used to form the clips from a sheet of metal. Conventional manufacturing methods are limited with regard to minimizing the space between the tines because the necessary manufacturing tolerances require that sufficient space be allowed for the manufacturing tools and/or processing materials.

Improved methods of manufacturing these types of clips and the clips resulting from them would make such clips more effective for many such uses.

SUMMARY OF THE INVENTION

The present invention is directed to methods for manufacturing tissue engaging clips in a manner in which a clip-precursor is first formed and such precursor is then reconfigured into the final shape of the clip. In a preferred embodiment of the invention, a clip having an annular or hoop-shaped generally planar configuration with radially inwardly extending tines is manufactured by first forming a precursor with the tines extending radially outward and then reconfigured by inserting the precursor to its final shape with the tines extending radially inward and then heat setting the clip in this configuration. This permits the tines to be packed more closely together which enhances the sealing function of the clip and reduces the size of the clip's footprint. As will be explained in more detail herein, this manufacturing method overcomes the limitations of conventional methods in which the clip is manufactured in its final configuration.

In another preferred embodiment, an annular or hoop-shaped planar clip precursor with radially inwardly extending tines is first manufactured in an oversize configuration and then has its lateral dimensions reduced to pack the tines closer together and to reduce the footprint of the clip and then heat set in that configuration.

BRIEF DESCRIPTION OF THE DRAWINGS

To further clarify the above-recited and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE INVENTION

The clips manufactured according to the present invention are useful for engaging tissue so as to connect tissue segments together or to close and/or seal openings through tissue such as a puncture wound in a body lumen. These clips may be used by deforming them from their generally planar configuration such that the tines are pointing in a direction generally transverse to the plane, holding the clip in this deformed condition, deploying the clip proximal to the tissue to be engaged and removing the deforming force such that the clip engages the tissue and attempts to return to its original generally planar configuration. The methods and apparatus disclosed in the above-mentioned U.S. patent application Ser. Nos. 10/081,726 and 09/732,178 can be used to deploy the clips of the present invention to engage tissue and close or seal an opening.

In such use, the deformation of the clip causes the tines to be directed generally axially away from the body of the clip and it is the elastic property of the deformed clip which causes it to attempt to return to its original generally planar configuration. The body of the device may comprise a series of looped elements which generally define an endless zigzag pattern, e.g., a sinusoidal pattern, extending about a central access. The looped elements are believed to facilitate deforming the device between the planar and transverse configurations, e.g., by distributing stresses through the device and minimizing localized stresses in the curved regions.

In a first preferred embodiment of the present invention, a clip precursor is first formed from a sheet of material, preferably a superelastic alloy, such as a nickel-titanium alloy ("Nitinol") alloy. The property of superelasticity and of certain alloys which possess that property is disclosed in U.S. Pat. No. 4,665,906 which is incorporated by reference herein.

Figure 1A:
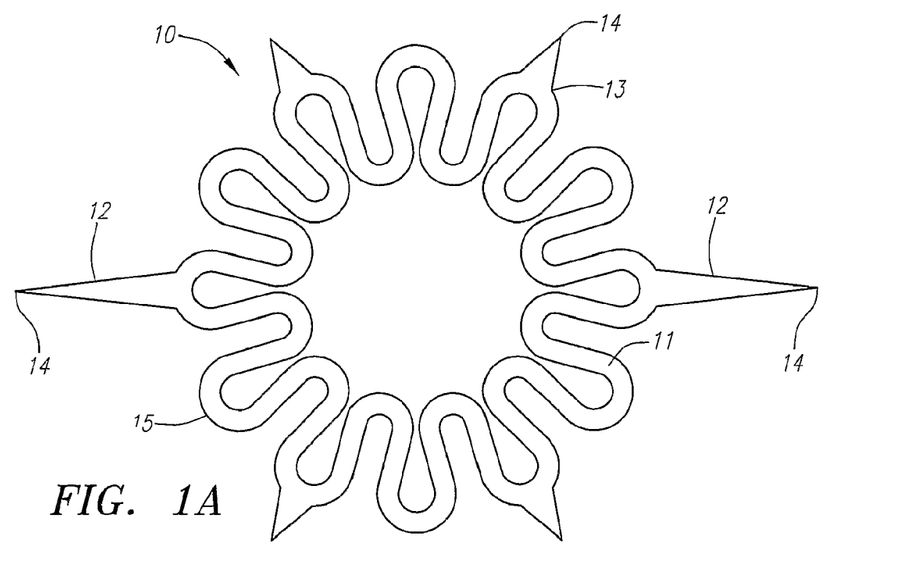
FIGS. 1A and 1B illustrate the before and after configuration of a clip manufactured according to one embodiment of this invention.

This forming can be done by removing portions of the material by cutting, chemical etching, laser cutting, photochemical etching, stamping, electrical discharge machining and the like to produce a precursor such as that shown in FIG. 1A which has radially outward extending tines.

The precursor can then be polished using one or more processes such as electropolishing, tumbling, sand blasting, sanding and the like or such polishing can be done as a final step after the clip is formed. Forming of a precursor in this manner does not require working to tolerances as close as those which would be required if the clip was to be manufactured in its final configuration shown in FIG. 1B because the radially outwardly extending tines of the precursor shown in FIG. 1A are easily accessible by the forming tool whereas attempting to directly form the clip with radially inwardly extending tines which are closely spaced requires difficult high precision metal cutting. Thus, manufacture of a precursor which is then reconfigured to final clip shape permits the achievement of closer spacing between the elements of the final clip than would otherwise be achievable with conventional methods.

The precursor 10 comprises a hoop-shaped planar body 11 which has outwardly extending primary (longer) tines 12 and secondary (shorter) tines 13. For example, the primary tines may be 0.070 to 0.105 inches in length and the secondary tines may be 0.025 to 0.035 inches in length. Each of the tines terminates in a point 14. When the precursor 10 has been reconfigured into clip 16 shown in FIG. 1B, the tines 12 and 13 become the tissue engaging portions of the clip. The tines may be sharpened or given a shape, e.g., barbs (not shown), while the device is in the precursor state. The body 11 may compromise connecting links such as loops 15. These links may have any suitable shape provided that such shape does not interfere with inversion of the precursor 10.

Figure 1B:
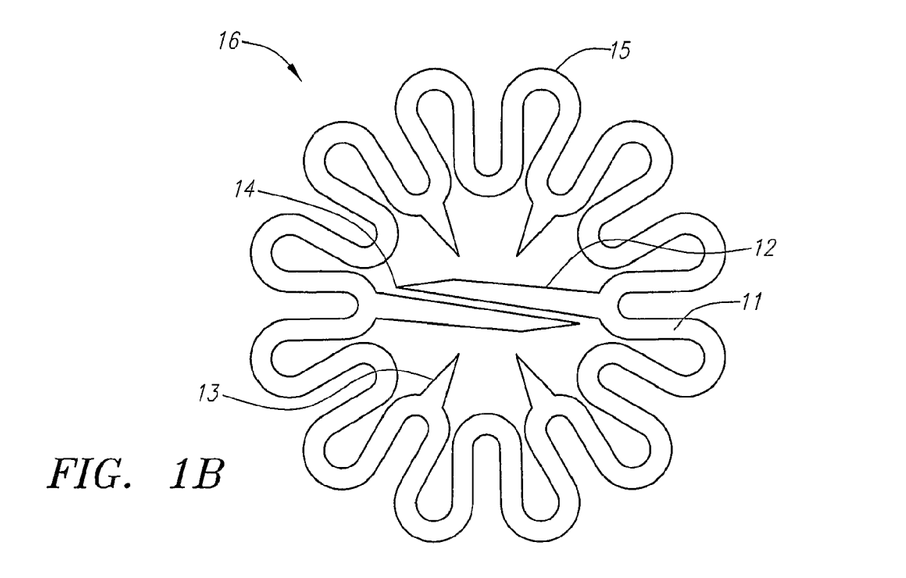

The precursor 10 is then inverted to reconfigure it into the shape of clip 16. In this preferred embodiment in which the precursor is formed from a sheet of nickel-titanium alloy, the inverted precursor is then heat set, e.g., by heating to a temperature of 510° C., and then quenched to cool to room temperature. The clip 16 will now be in the austenitic state.

Heat setting and quenching are essential to successful practice of the invention with superelastic alloys. As explained in more detail in U.S. Pat. No. 4,665,906, a superelastic alloy such as nickel-titanium exists in two states, the austenitic state and the martensitic state.

Such alloys will initially be in the austenitic state, e.g., when the precursor is formed.

However, when the precursor is inverted to take the shape of the final clip, the stress experienced by the alloy during the inversion will cause the alloy to be partially or wholly converted to the martensitic state. Such a martensitic state is commonly referred to as stress-induced martensite. Such martensite structure has the property of superelasticity and the inverted precursor would revert to its original shape if not held in the inverted configuration.

Since, if the inverted precursor was left in the martensitic state, it would want to elastically revert to its original uninverted state, it must be converted back to austenite. Thus, heating and quenching are required to convert the inverted precursor from the martensitic state to the austenitic state such that the clip is stable in its planar configuration as shown in FIG. 1B and will retain that configuration.

The times and temperatures for heat setting of superelastic alloys of various compositions can be determined from existing literature or can be determined empirically without any difficulty. The clips are small in size and the heating and quenching may be done with any conventional heating and quenching equipment. For example, once inverted, the inverted precursor can be held in that configuration and placed in a fixture which will hold it in the inverted configuration during heat setting.

When clips are manufactured according to the present invention, the space between the tines may actually be eliminated, i.e., after inverting the precursor, the tines may be in contact with each other, in either a side-by-side or an over-and-under relationship. The number, length and spacing of the tines may be varied according to the desires of the manufacturer.

Furthermore, while use of a planar precursor is a convenience in manufacturing, a planar configuration is not required. For example, the precursor could be bent along a diameter or major or minor axis of the precursor and could be heat set in such a bent configuration.

Figure 4:
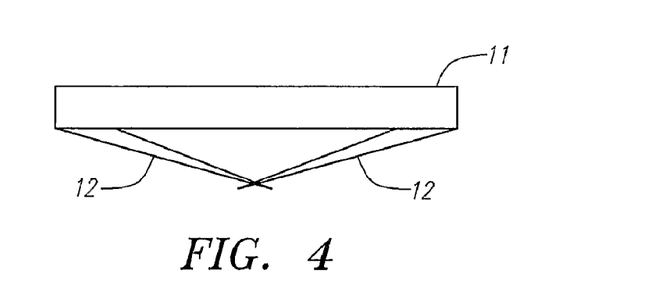
FIG. 4 illustrates a clip which, while generally planar, has tines which extend radially inwardly at an angle to the plane defined by the body.

Alternatively, the clip, while generally planar, may have the tines extending at an acute angle to the plane defined by the body as shown in FIG. 4 in which the body 11 and tines 12 are shown. Furthermore, manufacturing from a sheet of material is a convenience, but other manufacturing techniques, including joining of components such as the tines to the body, can be accomplished by welding, brazing, or other known methods of joining materials. In such cases, one or more of such components may be circular in cross-section or tubular in configuration.

Still further, the clip need not be fabricated from a single material, e.g., the tines may be manufactured from a different material than the body. In such cases, a portion of the clip such as the tines may be bioabsorbable provided that the final clip is capable of elastic recovery after being deformed. An advantage of the present invention is that it permits the production of clips with tines that are 30 to 40% or more longer than those which could be made with prior direct cutting methods, because there is no limit on the length of the tine which is formed on the precursor. Thus, after the precursor is inverted, the tines may overlap the annular body.

Figure 2A:
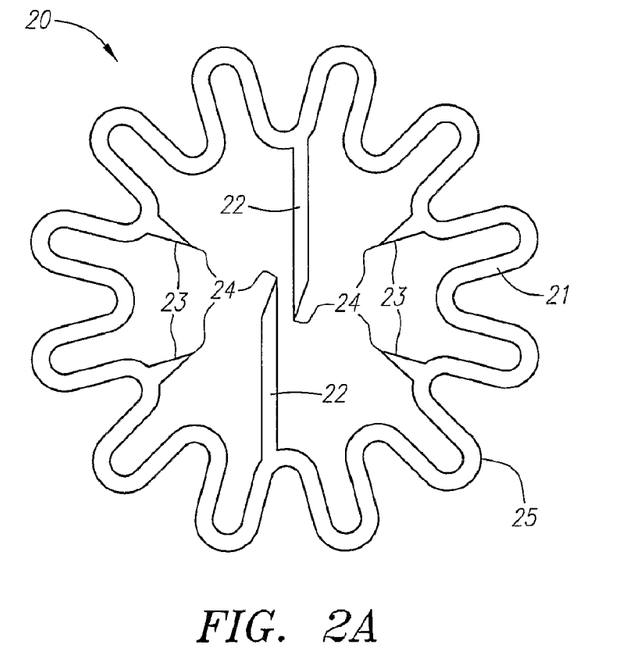
FIGS. 2A AND 2B illustrate the before and after-configuration of a clip manufactured according to another embodiment of the invention.
Figure 2B:
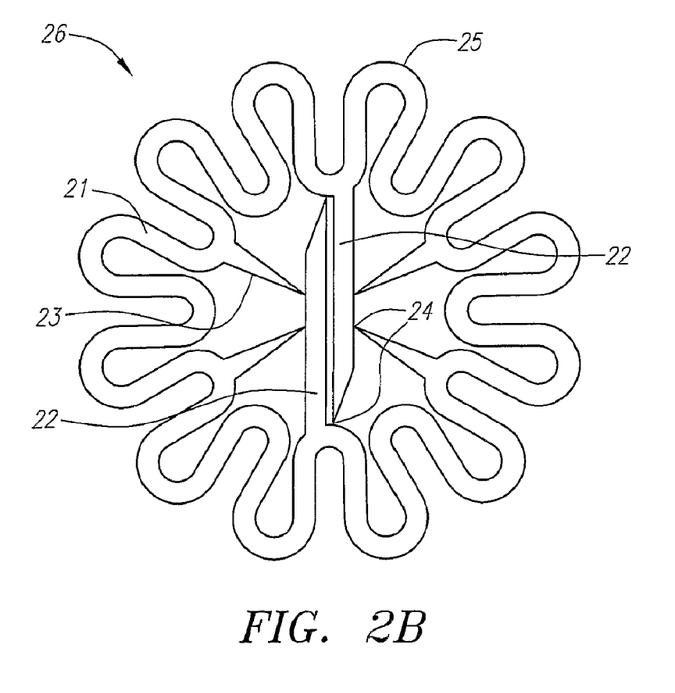

In the alternative embodiment of this invention illustrated in FIGS. 2A and 2B, the precursor 20 is manufactured in an expanded oversize configuration to provide space for removing material from a sheet of material, preferably a superelastic alloy such as nickel-titanium, by conventional methods such as cutting, chemical etching, photochemical etching, stamping, electric discharge machining, laser cutting or the like.

The precursor 20 is reconfigured by imposing radially inwardly directed force on body 21 such that precursor 20 takes a smaller planar shape such as one of those shown in FIG. 2B.

The precursor 20 has a planar body 21, tines 22 and 23 having points 24 and such tines are connected by links 25 as previously described with regard to FIG. 1A. The reconfigured precursor is then heat set and quenched as described above to complete the manufacture of clip 26.

Figure 3A:
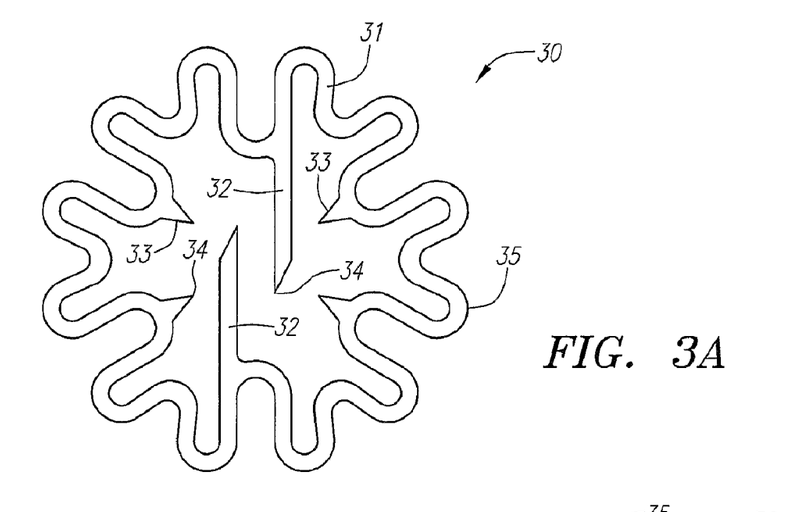
FIG. 3A-3C illustrate alternate before and after-configurations of clips manufactured according to the method of this invention in which the before configuration is that of FIG. 2A.
Figure 3B:
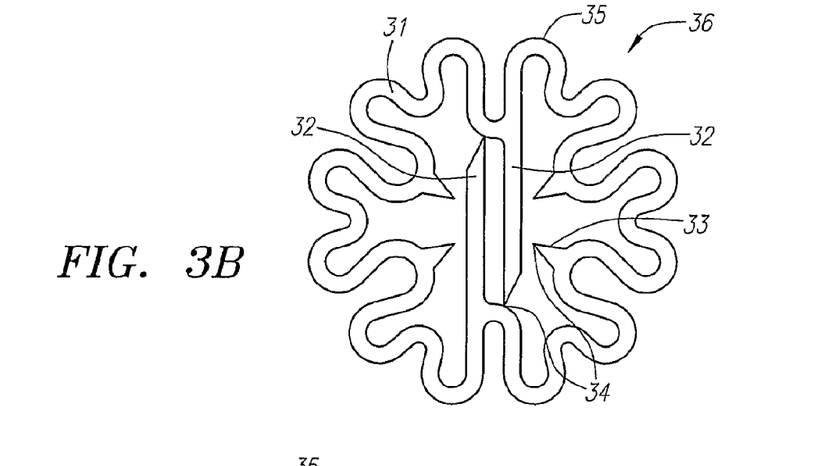
Figure 3C:
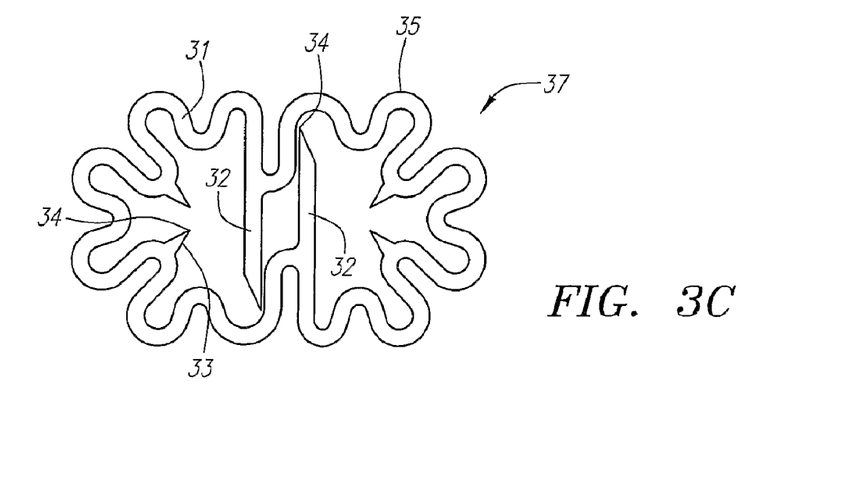

Clips of still other configurations can be manufactured in the manner of clip 26 by starting with a differently shaped precursor such as precursor 30 shown in FIG. 3A. Precursor 30 can be reconfigured by being subjected to radially inward deforming forces as shown in FIG. 3B or by opposed laterally inward forces as shown in FIG. 3C. In each case, the planar body 31 having tines 32 and 33 with points 34 and links 35 will be caused to take a smaller dimension and will be heat set as described above to form clips 36 and 37. Clips manufactured according to the method of the present invention can have a multitude of configurations other than those shown in FIGS. 1B, 2B, and 3B and 3C. For example, the configurations shown in U.S. patent application Ser. Nos. 09/732,178 and 10/081,726 could be manufactured according to the present invention.

Figure 7:
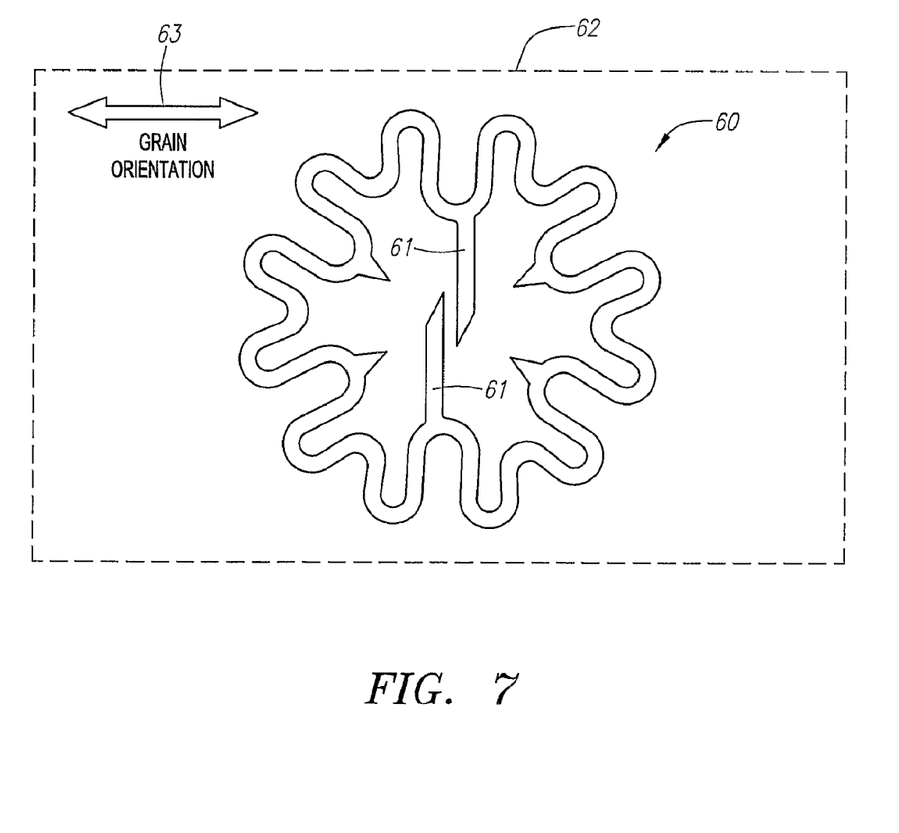
FIG. 7 illustrates the preferred relationship between the grain orientation of a nitinol sheet and the primary tines of a clip precursor.

It has been found that nitinol sheet is stronger in one direction than in others, which may be the result of crystal orientation in the nitinol. It is preferred to form the clip precursors such that the primary tines are aligned with the strongest orientation of the nitinol. It has been found, as shown in FIG. 7, that the greatest strength of the primary tines is achieved if those tines are transverse to the grain orientation of the nitinol. Thus, FIG. 7 illustrates clip precursor 60 having primary tines 61 as the precursor would be cut from sheet 62. The grain orientation of sheet 62 is shown by the double-headed arrow 63. Typically, a plurality of precursors 60 would be cut from the same sheet, each with its primary tines transverse to the grain orientation of the sheet. In addition, even if clips are formed directly without using precursors, it is desirable that their primary tines be transverse to the grain orientation.

Figure 5:
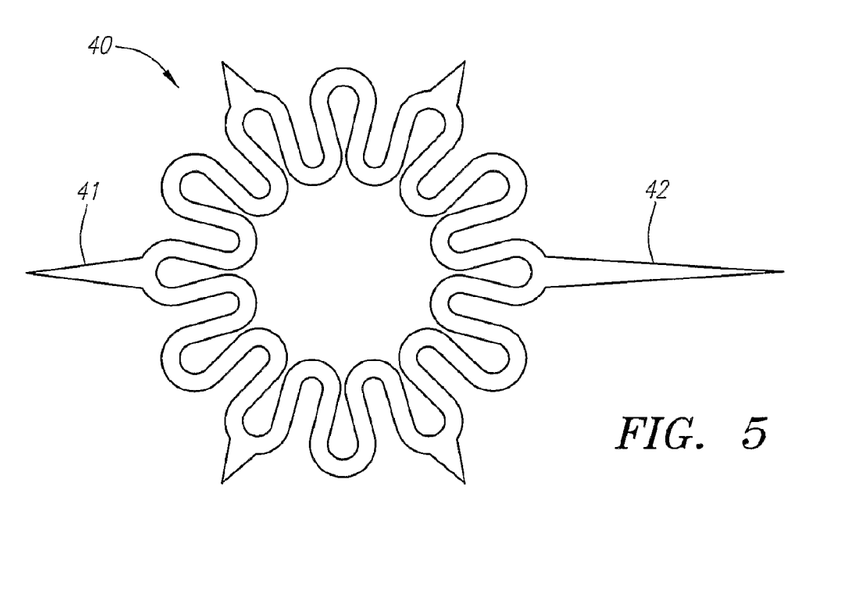
FIGS. 5 and 6 illustrate clip precursors in which radially opposed primary tines have different lengths.
Figure 6:
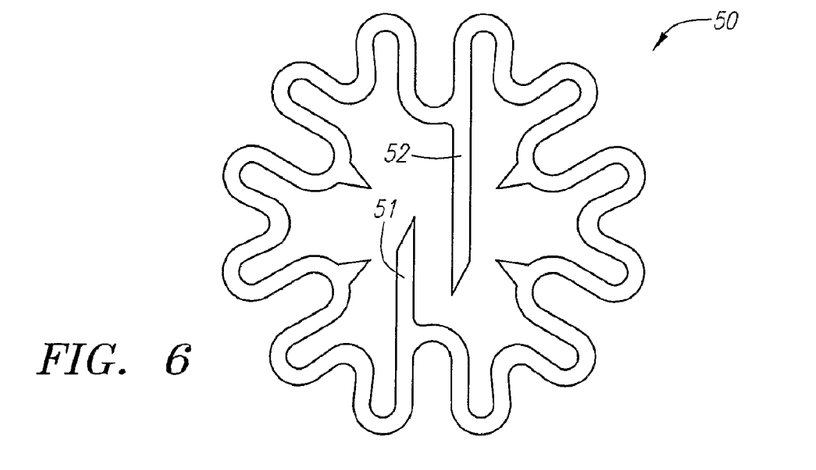

The clips of the present invention may have primary or secondary tines which have the same or different lengths and the tines may be straight or curved. For example, radially opposed tines may have one tine at "12 o'clock" which is longer than the opposing tine at "6 o'clock." Exemplary configurations of clip precursors with primary tines of different length are shown in FIGS. 5 and 6. In FIG. 5, clip precursor 40 is shown with a primary tine 41 which is shorter than primary tine 42. Similarly, in FIG. 6, a clip precursor 50 is shown which has a primary tine 51 which is shorter than primary tine 52.

The clips of the present invention may also be delivered using the apparatus and methods described in U.S. patent application Ser. No. 10/081,273, filed Feb. 21, 2002 which is assigned to the assignee of the present application and the disclosure of which is incorporated by reference herein. Similarly, the apparatus and methods disclosed in U.S. patent application Ser. No. 10/081,717, filed Feb. 21, 2002, which is assigned to the Assignee of the present application and the disclosure of which is incorporated by reference herein, may be used.

Other features can be added to the clips including radio-opaque markers, and/or porous surfaces to promote tissue ingrowth or the clip may be coated in whole or in part with a bioabsorbable material and/or coated with a material containing a substance which is delivered to the patient for therapeutic, diagnostic or other purposes. Such coatings may comprise peptides, clotting factors or other materials designed to benefit the patient.

While the principal object of the present invention is to provide a manufacturing method which facilitates the production of clips having a small footprint, the present invention can also be used to make clips of larger dimensions since, no matter what methods are used to cut the precursor from a sheet of material, the ease of manufacture of even larger size clips is facilitated. Thus, the advantages of the present invention may be realized with regard to clips having larger sizes and clips having a variety of configurations.

Having fully described the present invention including a description of preferred embodiments, it is to be understood that the scope of this invention is not to be limited to those preferred embodiments, but is of the full scope of the appended claims.

What is claimed is:

1. A method of manufacturing a clip comprising the steps of:
    forming the precursor of a clip from a material comprising a superelastic alloy which has an austenitic state and a martensitic state, said precursor having a generally annular body which is generally planar and having one or more tines which extend radially inwardly from said body, said precursor having a lateral dimension which is substantially larger than that of the clip;
    compressing said precursor in a radially inward direction to bring said tines substantially closer together;
    heating said precursor in its compressed configuration to cause said alloy to become substantially austenitic; and
    quenching said heated precursor to form a clip which is substantially austenitic.

2. The method of claim 1 wherein said alloy is nickel titanium.

3. The method of claim 1 wherein said body comprises a plurality of looped elements.

4. The method of claim 2 wherein the nickel titanium has a grain orientation and at least two tines have a longitudinal dimension transverse to the grain orientation.

5. The method of claim 1 wherein, after compression, at least two tines are in side-by-side relationship.

6. The method of claim 1 wherein, after compression, at least two tines are in an over-and-under relationship.

* * * * *